United States Patent [19]
Abdulwahed et al.

[11] Patent Number: 6,017,846
[45] Date of Patent: Jan. 25, 2000

[54] HIGHLY ACTIVE AND SELECTIVE CATALYSTS FOR THE PRODUCTION OF UNSATURATED NITRILES, METHODS OF MAKING AND USING THE SAME

[75] Inventors: Mazhar Abdulwahed, Damascus, Syrian Arab Rep.; Khalid El Yahyaoui, Meknes, Morocco

[73] Assignee: Saudi Basic Industries Corporation, Saudi Arabia

[21] Appl. No.: 09/228,888

[22] Filed: Jan. 11, 1999

[51] Int. Cl.[7] .............................. B01J 23/00; B01J 23/32; B01J 23/58; B01J 23/02; B01J 23/48
[52] U.S. Cl. ........................ 502/300; 502/305; 502/306; 502/311; 502/312; 502/313; 502/317; 502/319; 502/321; 502/324; 502/330; 502/340; 502/344; 502/347; 502/353
[58] Field of Search .................... 502/300, 311, 502/305, 306, 312, 313, 317, 319, 321, 324, 330, 340, 344, 347, 353

[56] References Cited

U.S. PATENT DOCUMENTS

| | | | |
|---|---|---|---|
| 3,057,915 | 10/1962 | Riemenschneider et al. | 260/533 |
| 3,131,223 | 4/1964 | Smidt et al. | 260/597 |
| 3,240,805 | 3/1966 | Naglieri | 260/533 |
| 3,301,905 | 1/1967 | Riemenschneider et al. | 260/597 |
| 3,872,148 | 3/1975 | Umemura et al. | 502/311 |
| 4,040,978 | 8/1977 | Li | 252/437 |
| 4,062,885 | 12/1977 | Mekhtiev et al. | 260/465 |
| 4,148,757 | 4/1979 | Brazdil et al. | 252/432 |
| 4,190,556 | 2/1980 | Grasselli et al. | 502/311 |
| 4,250,346 | 2/1981 | Young et al. | 585/658 |
| 4,292,203 | 9/1981 | Milberger et al. | 502/311 |
| 4,339,355 | 7/1982 | Decker et al. | 252/464 |
| 4,405,498 | 9/1983 | Ebner | 252/432 |
| 4,423,281 | 12/1983 | Yamamoto et al. | 502/311 |
| 4,487,850 | 12/1984 | Li | 502/311 |
| 4,524,236 | 6/1985 | McCain | 585/658 |
| 4,547,484 | 10/1985 | Li | 502/311 |
| 4,568,790 | 2/1986 | McCain | 585/658 |
| 4,596,787 | 6/1986 | Manyik et al. | 502/312 |
| 4,600,541 | 7/1986 | Aoki et al. | 558/321 |
| 4,788,173 | 11/1988 | Glaeser et al. | 502/311 |
| 4,899,003 | 2/1990 | Manyik et al. | 585/313 |
| 5,049,692 | 9/1991 | Hatano et al. | 558/319 |
| 5,132,269 | 7/1992 | Sasaki et al. | 502/311 |
| 5,162,578 | 11/1992 | McCain, Jr. et al. | 562/512.2 |
| 5,198,580 | 3/1993 | Bartek et al. | 562/542 |
| 5,300,682 | 4/1994 | Blum et al. | 562/512.2 |
| 5,364,825 | 11/1994 | Neumann et al. | 502/311 |
| 5,688,739 | 11/1997 | Drenski et al. | 502/308 |
| 5,808,143 | 9/1998 | Karrer et al. | 502/353 |
| 5,821,192 | 10/1998 | Seely et al. | 502/353 |
| 5,866,502 | 2/1999 | Cirjak et al. | 502/353 |

FOREIGN PATENT DOCUMENTS

| | | |
|---|---|---|
| 0 032 012 B1 | 7/1981 | European Pat. Off. . |
| 0 294 845 A1 | 12/1988 | European Pat. Off. . |
| 0 407 091 A1 | 1/1991 | European Pat. Off. . |
| 0 475 351 A1 | 3/1992 | European Pat. Off. . |
| 0 480 594 A2 | 4/1992 | European Pat. Off. . |
| 0 518 548 A2 | 12/1992 | European Pat. Off. . |
| 0 573 713 B1 | 12/1993 | European Pat. Off. . |
| 0 620 205 A1 | 10/1994 | European Pat. Off. . |
| 0 627 401 A1 | 12/1994 | European Pat. Off. . |

OTHER PUBLICATIONS

Thorsteinson, et al., "The Oxidative Dehydrogenation of Ethane over Catalysts Containing Mixed Oxides of Molybdenum and Vanadium" *Journal of Catalysis*, vol. 52, pp. 116–132 (1978) Jul./Nov. 1977.

*Primary Examiner*—Mark L. Bell
*Assistant Examiner*—Patricia C. Hailey
*Attorney, Agent, or Firm*—Whitman Breed Abbott & Morgan LLP

[57] ABSTRACT

An improved catalyst for the production of unsaturated nitriles from their corresponding olefins, the catalyst composition having the atomic ratios described by the empirical formula $Bi_aMo_bV_cSb_dNb_eAg_fA_gB_hO_x$ and methods of using the same.

7 Claims, No Drawings

HIGHLY ACTIVE AND SELECTIVE CATALYSTS FOR THE PRODUCTION OF UNSATURATED NITRILES, METHODS OF MAKING AND USING THE SAME

BACKGROUND OF THE INVENTION

1. Field of the Invention

The present invention relates to new ammoxidation catalysts for the production of unsaturated nitriles starting from their corresponding olefins, in particular, for the production of acrylonitrile from propylene. More specifically, the present invention is directed to an improved ammoxidation catalyst containing niobium and silver as essential elements for enhancing the activity and selectivity of the catalyst system.

2. Description of Related Art

Several publications are referenced in this application. The references describe the state of the art to which this invention pertains and are hereby incorporated by reference.

A number of ammoxidation catalysts are known in this field such as those disclosed in U.S. Pat. Nos. 4,405,498; 5,688,739; 4,600,541 and European Patent Publication Nos. 00 32 012 B1; 05 73 713 B1; 04 75 351 A1. All of these publications relate to molybdenum catalyst systems.

It is known in the art that the bismuth-molybdenum system plays a role of electron donor/acceptor mechanisms for selective oxidation and ammoxidation. Therefore different mechanisms were proposed based on this property [Delmon et al. (New Development in Selective Oxidation by Heterogeneous Catalysis, Vol. 72, 1992, p. 399–413) and Encyclopedia of Chemical Technology (Kirk-Othmer, Vol. 1, 4th edition, page 358)]. In these mechanisms, molybdenum was shown to be responsible for oxygen and nitrogen uptake and insertion into the substrate, while bismuth plays the role of H-abstraction of the methyl group in the β position. Therefore, bismuth and molybdenum should be present on the catalyst surface in adjacent form in order to form the suitable active phase for this reaction.

It should be noted that a deficiency of bismuth on the catalyst surface leads to total oxidation reactions of the substrate.

It is also well known that antimony plays a role of a donor and thus could improve the selectivity of a catalytic system. Antimony can also play an additional role by isolating the vanadium active centers which are highly active towards oxidation reactions. This leads to minimizing the total oxidation reaction and directs the reaction towards the desired product.

Many catalysts have been disclosed for the foregoing reactions. One such catalyst is described in U.S. Pat. No. 4,062,885, where BiMoSbV systems were used as active elements. The catalyst was used for the preparation of phthalonitrile by the ammoxidation of ortho-xylene. The use of such catalysts for oxidation or ammoxidation reactions involving unsaturated aliphatic hydrocarbon is not mentioned.

U.S. Pat. No. 4,040,978 relates to a catalyst for a ammoxidation reaction containing bismuth molybdate mixed with other elements.

U.S. Pat. No. 4,405,498 relates to a catalyst for oxidation and ammoxidation reactions containing BiMoVSb with additional elements of groups IA, IIA, IVA, VA, VIA, IB, IVB and VIIB of the periodic Table of the Elements. The patent does not disclose the use of niobium. Although, silver was disclosed, experimental results for the catalyst with silver did not reflect any performance improvement.

U.S. Pat. No. 4,600,541 relates to a catalyst comprising FeBiMo and promoters such as Pd, Pt, Os and Ir.

More recently, European Patent Publication No. 0 475 351 A1 relates to a catalyst containing KFeSbMo which could be promoted by Nb and W. The best yield was achieved with a catalyst of the formula $Fe_{10}Sb_{10}Mo_9Bi_2K_{0.6}Ni_{5.5}W_{0.3}B_{0.75}P_{0.75}(SiO_2)_{70}$.

European Patent Publication No. 0 573 713 B1 relates to a catalyst comprising MoBiFeCoNiCr promoted with at least three other promoters of alkali metals, alkaline earth metals, rare earth metals, Nb, Tl and As, with Fe, Co, Ni and Cr as essential catalyst components.

U.S. Pat. No. 5,688,739 relates to a multi-component catalyst. The base of this catalyst is bismuth molybdenum. Germanium was added as an essential element.

None of the prior art references discloses or suggests catalysts which provide high performance for the selective production of unsaturated nitriles from their corresponding olefins. Accordingly, it would be desirable to produce an improved catalyst for use in the selective production of unsaturated nitrites from their corresponding olefins.

OBJECTS OF THE INVENTION

It is an object of the invention to overcome the above-identified deficiencies.

It is another object of the invention to provide a useful catalyst for the production of nitrites from their corresponding olefins, particularly for the production of acrylonitrile from propylene.

It is a further object of the invention to provide a process for the production of acrylonitrile at high yields by vapor phase catalytic ammoxidation of propylene in a fluidized or fixed bed reactor.

The foregoing and other objects and advantages of the invention will be set forth in or apparent from the following description.

SUMMARY OF THE INVENTION

The present invention relates to an improved catalyst for the production of unsaturated nitrites from their corresponding olefins, the catalyst including a catalytic composition having the atomic ratios described by the empirical formula set forth below:

$$Bi_aMo_bV_cSb_dNb_eAg_fA_gB_hO_x,$$

wherein
- A=one or more elements selected from groups VB (e.g., V, Nb, Ta), VIB (e.g., Cr, Mo, W), VIIB (e.g., Mn, Tc Re) or VIII (e.g., Fe, Co, Ni) of the periodic table;
- B=at least one alkali promoter selected from group IA (e.g, Li, Na, K) or IIA (e.g., Mg, Ca) of the periodic table;
- a=0.01 to 12;
- b=0.01 to 12;
- c=0.01 to 2;
- d=0.01 to 10;
- e=0.01 to 1;
- f=0.0001 to 2, preferably 0.0001 to 1;
- g=0 to 2, preferably, 0.01 to 1;
- h=0 to 1, preferably, 0.001 to 0.5; and
- x=the number of oxygen atoms required to satisfy the valency requirements of the elements present.

The numerical values of a, b, c, d, e, f, g, h and x represent the relative gram-atom ratios of the elements, respectively, in the catalyst composition, where x is a number required to satisfy the valence requirements of the other elements. The elements are present in combination with oxygen, preferably in the form of various oxides.

The present invention also relates to a process for the catalytic preparation of unsaturated nitrites from their corresponding olefins, preferably for the production of acrylonitrile or metha acrylonitrile by the reactions of propylene or isobutylene with molecular oxygen and ammonia at temperatures between 200 to 550° C., using the active and selective catalyst of the invention.

Other objects as well as aspects, features and advantages of the present invention will become apparent from a study of the present specification, including the claims and specific examples.

DESCRIPTION OF THE PREFERRED EMBODIMENTS

One aspect of the invention relates to an improved ammoxidation catalytic system for the production of unsaturated nitrites from their corresponding olefins, in particular, for the production of acrylonitrile from propylene. More specifically, the present invention is directed to an improved ammoxidation catalyst containing niobium and silver as essential elements for enhancing activity and selectivity of the catalyst system. The aim of the present invention is to incorporate a new element into the Bi/Mo system which can improve the catalyst performance. This is achieved by incorporating niobium and silver into a bismuth/molybdenum/vanadium/antimony catalyst system.

The improved ammoxidation catalytic system of the invention comprises the atomic catalyst composition described by the empirical formula set forth below:

$$Bi_a Mo_b V_c Sb_d Nb_e Ag_f A_g B_h O_x,$$

wherein

A=one or more elements selected from groups VB (e.g., V, Nb, Ta), VIB (e.g., Cr, Mo, W), VIIB (e.g., Mn, Tc Re) or VIII (e.g., Fe, Co, Ni) of the periodic table;

B=at least one alkali promoter selected from group IA (e.g, Li, Na, K) or IIA (e.g., Mg, Ca) of the periodic table;

a=0.01 to 12;
b=0.01 to 12;
c=0.01 to 2;
d=0.01 to 10;
e=0.01 to 1;
f=0.0001 to 2, preferably 0.0001 to 1;
g=0 to 2, preferably, 0.01 to 1;
h=0 to 1, preferably, 0.001 to 0.5; and
x=the number of oxygen atoms required to satisfy the valency requirements of the elements present.

Accordingly, the aim of this invention is to incorporate silver as a new element in the Bi/Mo/V/Sb/Nb system which is disclosed in our copending U.S. application Ser. No. 09/228,885 (Attorney Docket No. KR80576-90), filed concurrently herewith and hereby incorporated by reference, as a good catalyst for the ammoxidation reaction. The silver has the role of improving the performance of the catalyst.

The catalysts of the invention can be used with or without a support. Suitable supports for the catalysts include alumina, silica, titania, zirconia, zeolites, silicon carbide, Mo, carbide, molecular sieves and other micro/nonporous materials, and mixtures thereof. When used on a support, the supported catalyst usually comprises from about 10 to 50% by weight of the catalyst composition, with the remainder being the support material.

Another aspect of the invention relates to methods of using the catalyst system of the invention. More specifically, the invention relates to an improved method of producing unsaturated nitrites from their corresponding olefins.

One preferred embodiment of the invention relates to an improved process for the catalytic preparation of acrylonitrile or metha acrylonitrile by the reaction of propylene or isobutylene with molecular oxygen and ammonia at a temperature of between about 200 to 550° C. using the ammoxidation catalytic system of the invention.

Preferably, the process achieves a propylene conversion of at least 70%, more preferably at least 75%, even more preferably at least 80%, and most preferred at least 90% using the catalytic system of the invention.

Preferably, the selectivity in mol % to acrylonitrile is greater than 75%, more preferably greater than 80%. The yield of acrylonitrile in mol % is preferably greater than 50%, more preferably greater than 55%, even more preferably greater than 60% and most preferred greater than 65%.

EXAMPLES

The following examples are illustrative of some of the products and methods of making and using the same falling within the scope of the present invention. They are, of course, not to be considered in any way limitative of the invention. Numerous changes and modifications can be made with respect to the invention.

The basic catalyst of present invention is a mixed metal oxide catalyst, which can be prepared according to any procedure well known by one of ordinary skill the art. Methods used to prepare representative catalysts are given below.

The examples described below are illustrative only and are not considered to be in any way limiting to the methods used to make these catalysts. The catalysts of the examples were prepared by the methods described in U.S. Pat. No. 4,405,498.

As used in the following examples, the following terms are defined in the following manner:

1. "W/F" is defined as the weight of the catalyst in grams divided by the flow rate of reactant stream in ml/sec measured at S.T.P.

2. "Propylene ($C_3H_6$) conversion" is defined as:

$$\frac{\text{Mols } C_3H_6 \text{ in feed} - \text{mols } C_3H_6 \text{ in effluent}}{\text{Mols } C_3H_6 \text{ in feed}} \times 100\%$$

3. "Acrylonitrile (ACN) selectivity" is defined as:

$$\frac{\text{Mols ACN in effluent}}{\text{Mols } C_3H_6 \text{ converted}} \times 100\%$$

4. "Acrylonitrile (ACN) yield" is defined as:

$$\frac{\text{Mols ACN formed}}{\text{Mols } C_3H_6 \text{ in feed}} \times 100\%$$

Example 1

BiMoV$_{0.175}$Sb$_{0.35}$O$_x$/50% Silica

Part A 10.2 g of Sb$_2$O$_3$ was slurried in 20 ml water along with 3.18 g V$_2$O$_5$. The mixture was boiled until it formed a paste. The paste was then dried at 120° C. and calcined under airflow at 760° C. for 2 hrs.

Part B 97 g $Bi(NO_3)_3$ $5H_2O$ was dissolved in 184 ml water and 30 ml $HNO_3$ (concentrated). Separately, 28.78 g $MoO_3$ was dissolved in 72 ml water and 30 ml concentrated $NH_4OH$. The two solutions were mixed together and the pH was adjusted to 4 using $NH_4OH$. The mixture was then boiled ca. 2 hours, filtered and washed with ca. 1000 ml water.

Part C

The pH of 297 g of a silica solution 30% wt % was adjusted with $HNO_3$ to pH=2 to form Part C. Part A and Part B were then added to Part C. The mixture was stirred for several hours, then dried at 120° C. and calcined under airflow at 550° C.

Example 2
$BiMoNb_{0.1}V_{0.175}Sb_{0.35}O_x/50\%$ Silica

This catalyst was prepared according to the above described method. Niobium was introduced into the system using the required amount of niobium penta oxide to the molybdenum solution in Part B. However, any source of niobium could be used for the same purpose.

Example 3
$Ag_{0.001}BiMoNb_{0.1}V_{0.175}Sb_{0.35}/50\%$ Silica

The catalyst was prepared according to the method set forth in Example 2. Silver was introduced by impregnating 7.147 g of the catalyst of Example 2 in a solution of 0.0016 g of silver nitrate in 100 cc water. However, any source of silver could be used for the introduction of silver into the catalyst by any method. After impregnation, the catalyst was dried and heated to 550° C. for 4 hr under airflow.

Example 4
$Ag_{0.01}BiMoNb_{0.1}V_{0.175}Sb_{0.35}/50\%$ Silica

The catalyst was prepared according to the method of Example 3, however, 0.0158 g of silver nitrate was used for impregnation.

Example 5
$BiMoNb_{0.1}V_{0.9}Sb_{0.175}/50\%$ Silica

The catalyst was prepared according to the method of Example 1, however, the nominal amount of vanadium oxide and antimony oxide were reduced by half.

Example 6
$Ag_{0.0001}BiMoNb_{0.1}V_{0.09}Sb_{0.175}/50\%$ Silica

The catalyst was prepared as in Example 5, and impregnated in silver nitrate solution as in Example 3.

Catalyst Test:

The calcined catalysts of the above examples were crushed to 35–60 mesh fraction. The crushed catalysts were charged into a tubular fixed bed stainless steel reactor.

The reaction was carried out at 475° C. under atmospheric pressure with the following feed composition: propylene/$O_2$/$NH_3$/He=7.9/16.8/10/65.3 and a space velocity "W/F"" of 3 or 1.5 as shown in Table No. I.

Comparison:

After reaching the steady state, the reactor effluent was analyzed using a modern gas chromatograph (HP 6890), equipped with both FID and TCD detectors. HCN was collected for a given period of time and then titrated according to the methods described in the literature.

Activity results were calculated according to the equations given above. Results are summarized in Table I.

TABLE I

| Run No. | CATALYST[1] | W/F | Propylene Conversion | ACN Y | ACN S | ACCN Y | ACCN S | $CO_x$ Y | $CO_x$ S | HCN Y | HCN S |
|---|---|---|---|---|---|---|---|---|---|---|---|
| 1 | $BiMoV_{0.175}Sb_{0.35}O_x$ | 3 | 62.9 | 48.7 | 77.5 | 3.1 | 4.9 | 10.0 | 16.0 | 0.6 | 0.9 |
| 2 | $BiMoNb_{0.1}V_{0.175}Sb_{0.35}O_x$ | 3 | 77.4 | 67.9 | 87.7 | 2.6 | 3.4 | 5.3 | 6.9 | 0.3 | 0.3 |
| 3 | $BiMoNb_{0.1}V_{0.175}Sb_{0.35}O_x$ | 4 | 81.4 | 73.1 | 89.7 | 2.9 | 3.5 | 5.1 | 6.2 | n.m. | n.m. |
| 4 | $BiMoNb_{0.1}V_{0.175}Sb_{0.35}O_x$ | 6 | 85.4 | 75.0 | 87.8 | 4.0 | 4.7 | 5.9 | 6.9 | n.m. | n.m. |
| 5 | $BiMoNb_{0.1}V_{0.09}Sb_{0.175}O_x$ | 3 | 85.6 | 72.3 | 84.5 | 1.7 | 1.9 | 8.2 | 9.6 | 0.5 | 0.6 |
| 6 | $BiMoNb_{0.1}V_{0.175}Sb_{0.35}Ag_{0.001}O_x$ | 1.5 | 74.7 | 62.3 | 83.3 | 2.4 | 3.2 | 8.3 | 11.2 | 1.3 | 1.8 |
| 7 | $BiMoNb_{0.1}V_{0.175}Sb_{0.35}Ag_{0.001}O_x$ | 3 | 90.4 | 71.6 | 79.2 | 3.5 | 3.9 | 12.6 | 13.9 | 2.3 | 2.6 |
| 8 | $BiMoNb_{0.1}V_{0.175}Sb_{0.35}Ag_{0.01}O_x$ | 1.5 | 72 | 58.1 | 80.4 | 4.4 | 6.1 | 8.2 | 11.3 | 1.2 | 1.7 |
| 9 | $BiMoNb_{0.1}V_{0.175}Sb_{0.35}Ag_{5.01}O_x$ | 3 | 96.2 | 77.5 | 80.5 | 4.5 | 4.7 | 12.5 | 13.0 | 1.3 | 1.3 |
| 10 | $BiMoNb_{0.1}V_{0.09}Sb_{0.175}Ag_{0.001}O_x$ | 3 | 94.0 | 77.5 | 82.4 | 2.6 | 2.8 | 11.1 | 11.8 | 1.6 | 1.7 |

Comparing Run Nos. 2 and 7 and Run Nos. 5 and 10 in Table I, it is clear that the presence of small amount of silver substantially increases the activity in terms of conversion and acrylonitrile yield. Comparison between Run Nos. 7 and 9 shows that, the addition of slightly more silver further improves catalyst performance.

This clearly demonstrates that the presence of silver is essential in substantially enhancing the catalyst performance as claimed in the present invention.

The addition of silver to the BiMoNbVSb catalyst also promotes the $CO_x$ and HCN formation. However, the overall yield of acrylonitrile was in general improved. Therefore, it can be concluded that silver enhances the activity of this catalyst system for acrylonitrile production.

The above description of the invention is intended to illustrative and not limiting. Various changes or modifications in the embodiments described may occur to those skilled in the art. These can be made without departing from the spirit or scope of the invention.

We claim:

1. A catalyst system for the production of unsaturated nitrites from the corresponding olefins comprising a catalyst composition having the empirical formula:

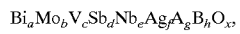

$Bi_aMo_bV_cSb_dNb_eAg_fA_gB_hO_x$, wherein

A is one or more elements selected groups VB, VIB, VIIB or VIII of the periodic table;

B is at least one alkali or alkaline earth metal promoter selected from groups IA or IIA of the periodic table;

a=0.01 to 12;

b=0.01 to 12;

c=0.01 to 2;

d=0.01 to 10;

e=0.01 to 1;

f=0.0001 to 2;

g=0 to 2;

h=0 to 1; and x=the number of oxygen atoms required to satisfy the valency requirements of the elements present.

2. The catalyst system of claim 1, wherein f is from 0.0001 to 1.

3. The catalyst system of claim 1, wherein said olefins are selected from propylene, isobutylene or mixtures thereof and said nitrites are selected from acrylonitrile, methacrylonitrile or mixtures thereof.

4. The catalyst system of claim 1, wherein said catalyst composition is supported on a catalyst support material selected from silica, alumina, zirconia, titania, alundum, silicon carbide, alumina-silica, inorganic phosphates, silicates, aluminates, borates and carbonates, pumice, montmorillonite, or mixtures thereof, thereby providing said catalyst system.

5. The catalyst system of claim 4, wherein said catalyst support material is silica.

6. The catalyst system of claim 1, wherein the catalyst system further comprises a support material and said catalyst system comprises from about 10–50% by weight catalyst composition with the remainder being the support material.

7. The catalyst system of claim 1, wherein g ranges from 0.01 to 1 and h ranges from 0.001 to 0.5.

* * * * *